United States Patent [19]

Hinman

[11] 4,412,064
[45] Oct. 25, 1983

[54] METAL ATOM CONTAINING EPOXY RESINS

[75] Inventor: P. Anthony Hinman, Torrance, Calif.

[73] Assignee: Armco Inc., Middletown, Ohio

[21] Appl. No.: 406,343

[22] Filed: Aug. 9, 1982

[51] Int. Cl.³ .............................................. C08G 79/00
[52] U.S. Cl. ....................................... 528/9; 525/364; 528/92
[58] Field of Search ....................... 528/9, 92; 525/364

[56] References Cited

U.S. PATENT DOCUMENTS

| | | | |
|---|---|---|---|
| 4,185,043 | 3/1981 | Shaffer | 525/364 |
| 4,256,868 | 1/1980 | Tarasen | 528/9 |
| 4,284,744 | 8/1981 | Shaffer | 528/9 X |
| 4,343,922 | 8/1982 | Shaffer | 528/9 X |

Primary Examiner—Lucille M. Phynes
Attorney, Agent, or Firm—Roylance, Abrams, Berdo & Farley

[57] ABSTRACT

It is disclosed that the properties of epoxy resins may be improved by incorporating therein at least one metal selected from the group consisting of boron, molybdenum, rhenium, tungsten and zirconium. The selection of a particular metal atom for incorporation into the epoxy resin or a combination of these metals will depend on the specific resin properties desired. The metal containing thermosetting resin is obtained by reacting an epoxy resin and one or more metal compounds selected from the following group:

(a) the reaction product of a polyol containing more than two hydroxy groups with boric acid;
(b) the reaction product of a polyol containing more than two hydroxy groups and a metal complex which is the reaction product of tungsten carbonyl with pyrrolidine;
(c) the reaction product of a polyol containing more than two hydroxy groups and a metal complex which is the reaction product of rhenium carbonyl with pyrrolidine;
(d) the reaction product of a polyol containing more than two hydroxy groups and a metal complex which is the reaction product of molybdenum carbonyl with pyrrolidine; and
(e) zirconium acetate.

10 Claims, No Drawings

METAL ATOM CONTAINING EPOXY RESINS

BACKGROUND OF THE INVENTION

This invention relates to thermosetting epoxy polymers containing one or more types of metal atoms chemically bonded in the polymer chain.

U.S. Pat. No. 4,185,043 to Robert C. Shaffer discloses thermoplastic and thermosetting polymers which incorporate tungsten carbonyl and/or molybdenum carbonyl metal atoms. The metal atoms are incorporated into the polymers by reacting a monomer or polymer containing at least one free carboxyl group with a reaction product of tungsten or molybdenum and pyrrolidine.

U.S. Pat. No. 4,256,868 to William L. Tarasen discloses epoxy resins containing chemically bonded metal atoms obtained by reacting an epoxy resin with a metal complex which is a reaction product of tungsten carbonyl and/or molybdenum carbonyl with pyrrolidine.

SUMMARY OF THE INVENTION

It has been discovered that the properties of epoxy resins may be improved by incorporating therein at least one metal selected from the group consisting of boron, molybdenum, rhenium, tungsten and zirconium. The selection of a particular metal atom for incorporation into the epoxy resin or a combination of these metals will depend on the specific resin properties desired. Thus, in accordance with the present invention, a metal containing thermosetting resin is obtained by reacting an epoxy resin and one or more metal compounds selected from the following group:

(a) the reaction product of a polyol containing more than two hydroxy groups with boric acid;

(b) the reaction product of a polyol containing more than two hydroxy groups and a metal complex which is the reaction product of tungsten carbonyl with pyrrolidine;

(c) the reaction product of a polyol containing more than two hydroxy groups and a metal complex which is the reaction product of rhenium carbonyl with pyrrolidine;

(d) the reaction product of a polyol containing more than two hydroxy groups and a metal complex which is the reaction product of molybdenum carbonyl with pyrrolidine; and (e) zirconium acetate.

The reaction products set forth in the foregoing subparagraphs (b), (c) and (d) are themselves novel compounds.

DETAILED DESCRIPTION OF THE INVENTION

Metals for incorporation into the epoxy resin system are prepared as prepolymers prior to their reaction with the epoxy polymer, except for zirconium which is introduced into the reaction as zirconium acetate. The prepolymers are prepared by reacting a polyol containing more than two hydroxy groups, such as glycerol, erythritol or sorbitol with boric acid, a molybdenium carbonyl/pyrrolidine complex, a rhenium carbonyl/pyrrolidine complex or a tungsten carbonyl/pyrrolidine complex.

The metal carbonyl/pyrrolidine complex may be prepared by one of several methods found in the literature, e.g., an article by Fowles et al entitled "The Reactions of Group VI Metal Carbonyls with Pyrrolidine, Piperazine and Morpholine", Inorganic Chemistry, Vol. 3, No. 2, February 1964, pages 257–259. The reaction product consisting of pyrrolidine-metal carbonyl complex is ground to a fine powder for subsequent reaction.

The amount of metal in the organometallic precursors may be varied by increasing or decreasing the amount of polyol used in the initial reaction with boric acid or the metal carbonyl/pyrrolidine complex. The maximum amount of boron is obtained when a 3:1 molar ratio of boric acid to glycerol is used. This ratio may be decreased from 3:1 in any increment to 1:3 boric acid:polyol depending on the percent boron desired in the prepolymer. In most cases, 160° C. is the desired reaction temperature.

The maximum amount of tungsten is obtained when a 1:2 molar ratio of tungsten carbonyl/pyrrolidine complex to polyol is used. The amount of tungsten may be decreased in any increment to a 1:4 molar ratio of tungsten carbonyl/pyrrolidine to polyol. In most cases, 190° C. is the desired reaction temperature.

The percentage of zirconium in the final epoxide is controlled by varying the amount of zirconium acetate reacted into the epoxy copolymerization. In the final copolymerization, the amount of zirconium acetate may range from 75% by weight down to 2% by weight depending on the desired metal content.

The epoxy resins which are suitable for use in this invention are well known in the art. An example is the diglycidyl ether of Bisphenol A, normally formed as a condensation product of epichlorohydrin and Bisphenol A (i.e., bis(4-hydroxyphenyl)dimethylmethane). Condensation products of epichlorohydrin with other polyhydric alcohols may also be used such as the diglycidyl ether of Bisphenol F (i.e., 4,4'-dihydroxybiphenyl). Other suitable epoxy resins include those derived from epoxidized glycerin dialiphatic esters, 1,4'-bis(2,3-epoxy-propoxy)benzene; 1,3-bis(2,3-epoxy-propoxy)benzene; 4,4'-bis(2,3-epoxy-propoxy)diphenyl ether; 1,8-bis(2,3-epoxy-propoxy)octane; 1,4'-bis(2,3-epoxypropoxy)cyclohexane; 4,4-bis(2-hydroxy-3,4'-epoxybutoxy)-2-chlorocyclohexane; 1,3-bis(2-hydroxy-3,4-epoxy-butoxybenzene) and 1,4-bis(2-hydroxy-4,5-epoxy-pentoxy)benzene.

A commercially available epoxy resin which has been successfully used in the practice of this invention is Epon 828, a viscous diglycidyl ether of bisphenol A having an epoxy equivalent weight in the range of 230–280 and a viscosity in the range of 15,000–22,500 centipoises at 25° C. Another commercially available epoxy resin which has been used is DOW DEN-438, a polyglycidyl ether of phenol-formaldehyde novolac having an epoxy equivalent weight in the range of 176–181 and a viscosity in the range of 35,000–70,000 centipoises at 52° C.

The epoxy resin is reacted with one or more of the metal compounds by combining the materials and heating the reaction mixture, preferably within the range of from about 75° to 150° C. The amount of metal compound which is reacted with the epoxy resin may vary widely, dependent on the desired properties of the cured resin. These include the percent metal desired in the final resin, specific atomic ratios of metals desired, char forming characteristics, oxidation resistance, energy absorption, desired cure temperature and other physical properties. Preferably, the final resin comprises from about 50% to in excess of 97% by weight epoxy resin. The metallic component of the resin is an integral part of the molecular structure of the resin and is therefore of atomic or near atomic size.

The metal containing epoxy resins of this invention are useful in a wide variety of applications, e.g., in the fabrication of coatings, composites, castings, as reimpregnation and/or laminating resins, foamed resins and other uses usually found for resin systems. They may be used in carbonaceous form. The presence of the metal atom in the basic epoxy resin molecule makes possible the formulation of epoxy resin matrix systems which are capable of absorbing large amounts of energy for specific related applications.

The metal containing epoxy resins of this invention have unique properties with regard to oxidation resistance when they are carbonized or graphitized and they may be used as the basic matrix in making carbon/carbon composites or for reimpregnation of carbon/carbon composites. When not carbonized, these resins also exhibit unique properties due to the incorporation of atomic metal in the backbone of the polymer chain. Both in carbonized and uncarbonized form, these resins exhibit unique energy absorption characteristics which are useful in many applications in the missile and aircraft industry.

Examples 1 to 5 which follow illustrate the procedures for preparing the metal compounds used in preparing the thermosetting epoxy resins, the preparation of which are illustrated in Examples 6 and 7.

EXAMPLE 1

Three moles of boric acid are reacted with one mole of glycerol and heated to 160° C. over a five hour period. A clear transparent prepolymer is produced. This is a thermoplastic material which is solid at room temperature.

EXAMPLE 2

One mole equivalent of molybdenum hexacarbonyl and an excess of pyrrolidine are reacted to form a metal pyrrolidine complex. At the completion of the reaction, the product is washed and ground to a fine powder. One mole of this complex and two moles of glycerol are reacted at approximately 145° C. for five hours and then held at 115° C. for an additional hour. A clear, dark amber material is obtained. This thermoplastic material is solid at room temperature.

EXAMPLE 3

One mole equivalent of rhenium carbonyl and an excess of pyrrolidine are reacted to form a rhenium/pyrrolidine complex. One mole of this complex and two moles of glycerol are reacted at approximately 135° C. for one hour and then solvated in dimethylformamide. The material is subsequently heated to 125° C. for about three hours. A clear, light amber material solvated in DMF is obtained.

EXAMPLE 4

One mole equivalent of tungsten hexacarbonyl and an excess of pyrrolidine are reacted to form a metal pyrrolidine complex. At the completion of the reaction, the product is washed and ground to a fine powder. One mole of this complex and two moles of glycerol are reacted at a temperature of approximately 145° C. for five hours and heated to 190° C. for two hours. A clear, amber prepolymer is obtained. The resultant thermoplastic material is solid at room temperature.

EXAMPLE 5

One equivalent of zirconyl carbonate is reacted with an excess of two equivalents of acetic acid at approximately 60° C. for four hours. The product, zirconium acetate, is subsequently heated in an air circulating oven at 98° C. for one hour, air dried 12 hours, and powdered in a mortar and pestle.

EXAMPLE 6

To 17.16 g of the boron prepolymer obtained in Example 1 there are added 67.49 g of the tungsten prepolymer obtained in Example 4 in a 500 ml resin kettle. The mixture is heated to 168° C. over a 45 minute period and thoroughly reacted. Then, 30.20 g of the reaction product are heated to 100° C. in a separate kettle with 5 ml of dimethylformamide (DMF). Another 10 ml of DMF and 45.30 g of Shell Epon 828 epoxy resin are added. The system is gradually heated to 145° C. with the addition of 165 ml of DMF, producing a copolymer solvated in approximately 54% DMF. Copolymerization occurs over a period of 5.25 hours. To 39.7 g of this copolymer, there are added 6.58 g of zirconium acetate obtained in Example 5 and 10 ml of DMF. The reaction mixture is heated to 118° C. at which time an additional 5.71 g of zirconium acetate and 10 ml of DMF are added. An additional 10 ml of DMF are added after the cook is stable at 112° C. The total cook time is approximately 1.25 hours. The resultant resin is a thermosetting epoxide with a curing temperature of about 125° C. It contains three metals chemically bonded into the epoxy resin, i.e., boron, tungsten and zirconium. The final copolymer exhibits properties of oxidation resistance and energy absorption and is suitable for lamination.

EXAMPLE 7

The boron prepolymer prepared in Example 1 (508.6 g) is solvated in approximately 800 ml of DMF. The solution is heated to 65° C. over a 30 minute period, at which time a similarly prepared solution of 640.84 g of Dow DEN-438 epoxy resin in 500 ml of DMF at 40° C. is added. The copolymerization occurs over a two hour period at a temperature of approximately 80° C. DMF (500 ml) is added during this period to maintain proper viscosity. The resultant resin is a thermosetting epoxide with a curing temperature of about 200° C. The copolymer exhibits oxidation resistance and is suitable for lamination.

The thermosetting metal containing epoxy resins of this invention may be cured under a variety of conditions. Thus, the resin may be heated to obtain a cure or it may be mixed with an amine hardener. Epoxy hardening agents are well known in the art and any such agent which is normally used to cross link an epoxy resin, such as a polyfunctional amine, a polyfunctional amine adduct, a blocked amine, e.g., ketimine or a polyamine may be used. The specific curing times and temperatures will depend upon the desired physical state of the resin and the particular use or treatment of the product. Thus, a coating resin would be cured, neat, in an oven, while a composite part would be cured in a hot press.

I claim:

1. A metal containing thermosetting epoxy resin obtained by reacting an epoxy resin and one or more metal compounds selected from the following group:
    (a) the reaction product of a polyol containing more than two hydroxy groups with boric acid;

(b) the reaction product of a polyol containing more than two hydroxy groups and a metal complex which is the reaction product of tungsten carbonyl with pyrrolidine;

(c) the reaction product of a polyol containing more than two hydroxy groups and a metal complex which is the reaction product of rhenium carbonyl with pyrrolidine;

(d) the reaction product of a polyol containing more than two hydroxy groups and a metal complex which is the reaction product of molybdenum carbonyl with pyrrolidine; and (e) zirconium acetate.

2. A metal containing thermosetting epoxy resin as defined in claim 1 wherein said polyol is glycerol, erythritol or sorbitol.

3. A metal containing thermosetting epoxy resin as defined in claim 1 wherein said metal compound comprises the reaction product of a polyol with boric acid.

4. A metal containing thermosetting epoxy resin as defined in claim 1 wherein said metal compound comprises the reaction product of a polyol and a metal complex which is the reaction product of tungsten carbonyl with pyrrolidine;

5. A metal containing thermosetting epoxy resin as defined in claim 1 wherein said metal compound comprises the reaction product of a polyol and a metal complex which is the reaction product of rhenium carbonyl with pyrrolidine;

6. A metal containing thermosetting epoxy resin as defined in claim 1 wherein said metal compound comprises the reaction product of a polyol and a metal complex which is the reaction product of molybdenum carbonyl with pyrrolidine.

7. A metal containing thermosetting epoxy resin as defined in claim 1 wherein said metal compound comprises zirconium acetate.

8. A thermosetting epoxy resin containing chemically bonded boron atoms.

9. A thermosetting epoxy resin containing chemically bonded rhenium atoms.

10. A thermosetting epoxy resin containing chemically bonded zirconium atoms.

* * * * *

UNITED STATES PATENT AND TRADEMARK OFFICE
CERTIFICATE OF CORRECTION

PATENT NO. : 4,412,064
DATED : October 25, 1983
INVENTOR(S) : P. Anthony Hinman

It is certified that error appears in the above—identified patent and that said Letters Patent is hereby corrected as shown below:

On the title page, change the name of the Assignee from "Armco Inc., Middletown, Ohio" to --HITCO, Irving, California--.

Signed and Sealed this

Twenty-seventh Day of December 1983

[SEAL]

Attest:

GERALD J. MOSSINGHOFF

Attesting Officer   Commissioner of Patents and Trademarks